United States Patent [19]

Hansenne-Richoux et al.

[11] Patent Number: 5,330,758
[45] Date of Patent: Jul. 19, 1994

[54] PROCESS FOR PRODUCING A COSMETIC COMPOSITION FOR APPLICATION TO THE HAIR, COMPOSITION OBTAINED BY THIS PROCESS AND PROCESS FOR COSMETIC TREATMENT WITH THE AID OF THE SAID COMPOSITION

[75] Inventors: Isabelle Hansenne-Richoux, Paris; Marie-Pascale Audousset, Levallois-Perret, both of France

[73] Assignee: L'Oreal, Paris, France

[21] Appl. No.: 997,909

[22] Filed: Dec. 29, 1992

Related U.S. Application Data

[63] Continuation of Ser. No. 653,632, Feb. 12, 1991, abandoned.

[30] Foreign Application Priority Data

Feb. 23, 1990 [FR] France .................. 90 02301

[51] Int. Cl.5 .............................. A61K 37/22
[52] U.S. Cl. ..................... 424/450; 424/451; 424/456; 424/401; 424/62; 424/70; 424/47
[58] Field of Search ............... 424/450, 451, 456, 401, 424/62, 70, 47

[56] References Cited

U.S. PATENT DOCUMENTS

| | | | |
|---|---|---|---|
| 4,536,324 | 8/1985 | Fujiwara et al. | 252/311 |
| 4,608,211 | 8/1986 | Handjani et al. | 264/4.6 |
| 4,673,568 | 6/1987 | Grollier et al. | 424/47 |
| 4,772,471 | 9/1988 | Vanlerberghe et al. | 424/62 |
| 4,897,308 | 1/1990 | Vanlerberghe et al. | 428/402.2 |
| 5,055,228 | 10/1991 | Zabotto et al. | 252/312 |
| 5,089,269 | 2/1992 | Noda et al. | 424/456 |
| 5,118,507 | 6/1992 | Clement | 424/401 |

FOREIGN PATENT DOCUMENTS

| | | |
|---|---|---|
| 0155806 | 9/1985 | European Pat. Off. . |
| 0283165 | 2/1988 | European Pat. Off. . |
| 2315991 | 6/1975 | France . |
| 2597367 | 4/1986 | France . |

*Primary Examiner*—Thurman K. Page
*Assistant Examiner*—William E. Benston, Jr.
*Attorney, Agent, or Firm*—Cushman, Darby & Cushman

[57] ABSTRACT

Cosmetic composition containing at least one silicone, a lipid and water, in which the lipid is a nonionic amphiphilic lipid. The composition is prepared with the aid of a known process for producing nonionic vesicles, in which the nonionic amphiphilic lipid and the silicone are mixed before the process for forming the nonionic vesicles. At least one cationic surface-active agent is preferably introduced into the aqueous dispersion phase after formation of the vesicles.

14 Claims, No Drawings

PROCESS FOR PRODUCING A COSMETIC COMPOSITION FOR APPLICATION TO THE HAIR, COMPOSITION OBTAINED BY THIS PROCESS AND PROCESS FOR COSMETIC TREATMENT WITH THE AID OF THE SAID COMPOSITION

This is a division of application Ser. No. 07/653,632, filed Feb. 12, 1991, now abandoned.

The present invention relates to a process for producing a cosmetic composition for application to the hair, the cosmetic composition obtained by this process and a process for cosmetic treatment with the aid of the said composition.

It is well known that the hair is made sensitive or fragile to varying degrees under the effect of atmospheric agents and/or certain cosmetic treatments, such as perming, dyeing or bleaching. Hair which has been made sensitive or fragile becomes difficult to untangle and to style both in the wet and dry state. Moreover, it is rough to the touch, no longer appears smooth or shiny and is charged with static electricity.

Attempts have therefore been made to apply to the hair compositions which make it possible to remedy these different problems.

It has been known for a very long time to use oils and fatty substances to restore softness and shine to the hair; the application of these compounds is generally followed by shampooing in order to remove the excess oil or fatty substance from the hair. However, the use of oils and fatty substances softens the hair and makes it heavier and consequently it is impossible to obtain a hairstyle with hold and body.

It has already been proposed to use compositions containing silicone oils. Those make it possible to obtain shining hair, but prolonged use or use in large quantities has the drawback of giving the hair a greasy appearance.

Aqueous compositions containing cationic surface-active agents are currently being used; these are applied to the hair and left to act for several minutes before the hair is rinsed. The cationic surface-active agents improve untangling and styling, but have drawbacks: they have a tendency to make the hair heavy and to give it a greasy appearance. Moreover, the hair has a tendency to become dirty again rapidly. These drawbacks are accentuated all the more the finer and more sensitive the hair being treated is.

It is also known to use compositions containing both cationic surface-active agents and oils or fatty substances. These compositions can have good cosmetic and rheological properties, but they have a tendency to form a deposit on the hair. In order to prevent the formation of this deposit, it has been proposed to use compositions containing silicones in addition to the fatty substances and the surface-active agents. In particular, in the document EP-A-0 155 806 an aqueous composition is described which contains linear polydimethylsiloxanes, polydimethylsiloxanes modified by at least one polyalkylene oxide (dimethicone copolyalcohols), a lipidic vehicle and a cationic surface-active agent; this composition is prepared by simple mixing in hot water, cooling and agitation.

It is also known that, by agitation in the presence of an aqueous phase, certain amphiphilic lipids are capable of forming a lamellar hydrated lipidic phase leading to vesicles French Patent No. 2 315 991 describes in particular the case where the amphiphilic lipid is a nonionic lipid. These vesicles consist of concentric layers of lipid(s) separated by layers of internal aqueous phase. The nonionic lipid(s) used is (are), in a known manner, amphiphilic lipids of natural or synthetic origin having one (or several) long hydrocarbon chain(s) per molecule. The numerous processes for producing the vesicles of nonionic lipids are well known. In one first type of process (see in particular US-A-4 772 471) the amphiphilic lipids are dissolved in a solvent, then a film is formed by evaporating the solvent; next the film obtained is placed in contact, whilst agitating, with the aqueous phase to be encapsulated, bud all of this is subjected to energetic agitation. In a second type of process (see in particular FR-A-2 315 991) the use of a solvent is avoided: in a first stage the melted nonionic amphiphilic lipid(s) (for example at 70°–95° C.) is (are) placed in contact with the aqueous phase to be encapsulated in order to form a hydrated lamellar phase, and the addition of the aqueous phase to be encapsulated is continued under strong agitation until vesicles are formed; in a second stage an aqueous dispersion phase, which may be identical to or different from the aqueous phase to be encapsulated, is added whilst continuing the agitation.

According to the present application, it has been found that the characteristics of treatment of the hair with the aid of an aqueous composition containing silicones and lipids are improved when the lipids used are nonionic amphiphilic lipids which are capable for forming vesicles and the composition is prepared with the aid of a known process for producing nonionic vesicles in which the nonionic amphiphilic lipid and the silicone are mixed before the process of forming the vesicles.

It has been verified, notably by electron microscopy, that the composition prepared in this way contains stable vesicles.

It has been shown by comparative tests that the use of nonionic amphiphilic lipids which are capable of forming vesicles makes it possible to obtain better results than the use of nonionic lipids which do not form vesicles and that the fact that the silicone is introduced into the nonionic amphiphilic lipid before the process of forming the vesicles also makes it possible to obtain better results than when the silicone is introduced into the aqueous dispersion phase of the vesicles before the formation of the vesicles.

The prime object of the present invention, therefore, is to provide a process for producing a cosmetic composition for application to the hair containing at least one lipid, at least one silicone and water, characterised in that at least one nonionic amphiphilic lipid which is capable of forming vesicles with at least one silicone is mixed with the water, this mixture is subjected to a process for forming vesicles encapsulating an aqueous phase, and the product obtained is dispersed in an aqueous dispersion phase.

The aqueous dispersion phase preferably contains at least one cationic surface-active agent.

The process used for forming vesicles is preferably the process which does not require any solvent, in which the mixture of nonionic amphiphilic lipid(s) and silicone(s) is melted, an aqueous phase to be encapsulated is introduced in such a way as to form a hydrated lamellar phase, the addition of this phase is continued under energetic agitation in order to form vesicles, then an aqueous dispersion phase is added.

It is also possible to use the process in which the nonionic amphiphilic lipid(s) and the silicone(s) are dissolved in an organic solvent, in which the solvent is evaporated in the receptacle in which the solution is placed in order to form of a film of the (lipid(s)-/silicone(s)) mixture on the walls of the said receptacle, the aqueous phase to be encapsulated is added into the said receptacle whilst agitating energetically until vesicles are formed, and finally an aqueous dispersion phase is added.

The nonionic amphiphilic lipid used according to the present invention is preferably chosen from the group formed by the linear or branched ethers and esters of polyglycerol of formula (I):

     (I)

in which $-C_3H_5(OH)O-$ represents the following in a mixture or separately:

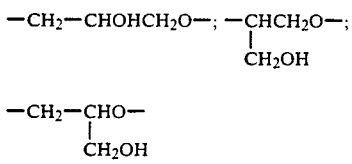

in which $\overline{n}$ is a mean statistical value between 2 and 6 in which R is:

a) either an aliphatic chain $R_1$ or an $R_2CO$ radical, $R_1$ being a linear or branched $C_{12}-C_{18}$ aliphatic radical and $R_2$ being linear or branched $C_{11}-C_{17}$ aliphatic radical;

b) or $R_3+O-C_2H_3(R_4)+$ where $-OC_2H_3(R_4)-$ is represented by the following structures in a mixture or separately:

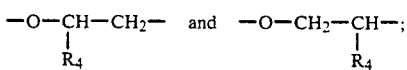

$R_3$ being an $R_1$ or $R_2CO$ radical;

$R_4$ being an $R_1$ radical, $R_1$ and $R_2$ having the meanings given dove.

In a known manner the nonionic amphiphilic lipid(s) constituting the lamellar lipidic phase is (are) preferably associated with at least one stabilising additive intended to modify the permeability or the surface charge of the lipidic layers. According to the invention these additives are more particularly chosen from amongst the sterols and/or the anionic stabilisers. The sterol can advantageously be cholesterol or betasitosterol a weight-for-weight mixture of nonionic amphiphilic lipid(s) and cholesterol or a mixture containing less than 50% by weight of cholesterol is preferably used. The anionic stabiliser is advantageously chosen from amongst the monosodium or disodium salts of acylglutamate, the acyl radical having from 14 to 22 C atom, such as the salt of stearyl monosodium glutamate, the disodium salts of cocoyl and stearyl glutamates or of the mixture of acyl radicals of copra and tallow; and the phosphoric acids of fatty alcohols having 12 to 16 C atoms; the anionic stabilisers are associated with the nonionic amphiphilic lipid(s) in a quantity not generally exceeding 12% by weight with respect to the weight of the nonionic amphiphilic lipid(s). In a known manner, it is possible to add both a sterol and an anionic stabiliser to the nonionic amphiphilic lipids.

The silicone(s) mixed with the nonionic amphiphilic lipids according to the invention is (are) advantageously chosen from amongst the:
polydimethylsiloxanes and their mixtures with a trimethylsiloxysilicate;
polydimethylsiloxanes modified by hydroxyl groups at the end of the chain;
polydimethylsiloxanes modified by $C_{12}-C_{22}$ alkoxy groups;
polydimethylsiloxanes modified by polyoxyalkylene groups, the alkylene radical having 2 or 3 C atom;
polydimethyl siloxanes modified by acyloxyalkyl radicals in which the acyl radical has 12-22 C atoms and the alkyl radical has 1-4 C atom;
polydimethyl phenylsiloxanes, polymethylalkyl (C 1-$C_{20}$)siloxanes); polymethyl[alkyl($C_1-C_4$)aryl]siloxanes modified by alkyl ($C_1-C_4$)amine groups; and cyclopolysiloxanes.

Amongst the silicones which are advantageously used my be cited those sold under the following brand names:
"SILBIONE 47V500000" by "RHONE POULENC" (polydimethylsiloxane having a molecular weight of approximately 250000 );
"SILBIONE huile 70045V5" by "RHONE POULENC" (decamethylcyclopentasiloxane);
"FLUID DOW CORNING 593" by "DOW CORNING" or "SS 4267 SILICONE FLUID" sold by "GENERAL ELECTRIC CORP." (mixture of polydimethylsiloxane and trimethylsiloxysilicate);
"SILICONE COPOLYMER F 555" by "S. W. S. SILICONES CORP." (stearoxypolydimethylsiloxane);
"RHODORSIL HUILE 70633V30" by "RHONE POULENC" (polymethylphenyl siloxane);
"GP 7100 SILICONE FLUID" by "GENESEE POLYMERS CORP." (polymethyl (alkylaryl)-siloxane modified by alkylamine groups);
"VOLATILE SILICONE FZ 3109" sold by "UNION CARBIDE" (tetramethyltetraoctylcyclotetrasiloxane).

The silicones used can be in the form of oils, gum or resins which are insoluble in water and are or are not volatile.

At least one non-volatile silicone is preferably used, such as a polydimethylsiloxane oil hydroxylated at the end of the chain or a polyphenylmethylsiloxane gum, in the form of a solution in at least one cyclic volatile silicone oil of the cyclomethicone type.

More particularly, the following solutions are used:
15% by weight of a non-volatile polydimethylsiloxane such as that sold under the brand name "SILBIONE 47V50000" by "RHONE POULENC" in solution in 85% by weight of decamethylcyclopentasiloxane such as that sold under the brand name "VOLATILE SILICONE 7158" by "UNION CARBIDE";
13% by weight of a mixture of non-volatile polydimethylsiloxanes hydroxylated at the end of the chain such as that sold under the brand name "Q2 1401" by "DOW CORNING" in solution in 87% by weight of a mixture of decamethylcyclopentasiloxane and octamethylcyclotetrasiloxane;
15% by weight of a non-volatile phenylmethylsiloxane having a molecular weight of approximately 600000 in solution in 85% by weight of a mixture of decamethylcyclopentasiloxane and octamethylcyclotetrasiloxane.

The cationic surface-active agent which may be contained according to the invention in the aqueous dispersion phase is generally dispersed hot in the water. This phase is then mixed into the dispersion containing principally the nonionic lipid and the silicone. The mixing is either carried out hot or at ambient temperature. The surface-active agent is advantageously a surface-active agent which is insoluble in water at ambient temperature. It is preferably at least a derivative of quaternary ammonium of formula II:

$$\begin{array}{c} R_5 \quad R_8 \\ \diagdown_{\oplus}\diagup \\ N \quad X^{\ominus} \\ \diagup \quad \diagdown \\ R_6 \quad R_7 \end{array} \quad (II)$$

in which X (is chlorine or $CH_3SO_4$ and $R_5$ is a $C_1$-$C_4$ alkyl radical, preferably the radical methyl, and in which:

either $R_6$ and $R_7$ are $C_1$-$C_4$ alkyl radicals, identical to or different from $R_5$ and each other, and $R_8$ is a $C_{20}$-$C_{22}$ radical;

or $R_6 = R_5$ and $R_7 = R_8 = C_{18}$ alkyl radical;

or $R_6$ designates an (alkyl and/or alkenyl) amidoethyl radical in which the alkyl and/or alkenyl radical has 13-21 C atoms and derives from the fatty acids of tallow and $R_7$ and $R_8$ form together with the nitrogen a 4,5-dihydroimidazole heterocycle which is substituted, notably in position 2, by an a $C_{13}$-$C_{21}$ alkyl and/or alkenyl radical.

The surface-active agent is more particularly a tetraalkylammonium chloride of formula (II), in which $R_5$, $R_6$ and $R_7$ are identical $C_1$-$C_4$ alkyl radicals, preferably methyl, and $R_8$ is a $C_{20}$-$C_{22}$ alkyl radical. Behenyltrimethylammonium chloride can advantageously be used.

It is also possible advantageously to use distearyldimethylammonium chloride, a compound of formula (II) in which $R_5 = R_6 = CH_3$ and $R_7 = R_8 = C_{18}$ alkyl.

When the surface-active agent is a methylsulphate it is advantageously the compound of formula III:

$$\left[ R_9-\overset{O}{\overset{\|}{C}}-NH-CH_2-CH_2-\underset{\underset{R_9}{\overset{|}{C}}\diagdown_N}{\overset{CH_3}{\overset{|}{N}}\diagup^{CH_2}_{CH_2}} \right]^{\oplus} CH_3SO_4^{\ominus} \quad (III)$$

in which $R_9$ designates a mixture of $C_{13}$-$C_{21}$ alkenyl and/or alkyl radicals derived from the fatty acids of tallow, for example the product sold under the brand name "REWOQUAT W 7500" by "REWO".

According to the present invention It is possible in a known manner to add to the nonionic amphiphilic lipid(s) and/or to the silicone(s), before the formation of the vesicles, at least one liposoluble cosmetic and/or pharmaceutical active substance which will be in the lipidic layers of the vesicles. It is also possible in a known manner to introduce into the aqueous phase to be encapsulated and/or into the aqueous dispersion phase at least one cosmetic and/or pharmaceutical active substance which is soluble in water and/or at least one additive. Amongst the active substances may be cited vitamin A acid, linoleic acid, tocopherols and agents to prevent hair loss or to restore growth of hair, anti-dandruff agents, retinoids or related agents, anti-inflammatories, anti-fungals, anti-seborrhoeics, sun filters or the like.

Amongst the additives may be cited preservatives, colourings, perfumes or the like. In particular, a thickener can be introduced in a known manner into the aqueous dispersion phase. The thickening agents are more particularly chosen from amongst the cellulose derivatives such as hydroxymethylcellulose, carboxymethylcellulose, hydroxybutylcellulose, hydroxypropylcellulose and more particularly hydroxyethylcellulose, such as the products sold under the brand name "NATROSOL" (150250) by "HERCULES" or "CELLOSIZE" (QP and WP) by "UNION CARBIDE" or "NATROSOL PLUS GRADE 330 CS" by "AQUALON", methylhydroxypropylcellulose, particularly the products sold under the name "METHOCEL" (E, F, J, K) by "DOW CHEMICAL" or heterobiopolysaccharides such as for example the xanthan gums marketed under the trade marks "KELTROL" and "KELZAN" by "KELCO", "RHODOPOL" and "RHODIGEL" by "RHONE POULENC" or "ACTIGUM" by "CEWCA/SATIA".

These thickening agents can be incorporated indiscriminately in compositions containing silicosomes either in the presence of or without a cationic surface-active substance.

When the compositions do not contain any cationic surface-active agent it is also possible to use as thickening agent reticulated polyacrylic acids such as the products sold under the brand name "CARBOPOL" by "GOODRICH" such as Carbopols 910, 934, 934P, 940, 941, 1342.

It is also possible in a known manner to introduce into the aqueous dispersion phase a substance which is not miscible in water, such as an oil.

The second object of the present invention is a composition obtained by the process defined above, comprising at least one silicone and at least one nonionic amphiphilic lipid in the form of vesicles dispersed in an aqueous dispersion phase also preferably containing at least one cationic surface-active agent.

The composition according to the invention advantageously contains, by weight with respect to the total weight of the composition:

1 to 10% of cationic surface-active agent(s);
1.5 to 20% of nonionic amphiphilic lipid(s);
0.5 to 10% of silicone(s);
and preferably:
1 to 7% of surface-active agents(s);
1.5 to 10% of nonionic amphiphilic lipid(s);
1.5 to 5% of silicone(s).

The composition according to the invention is in the form of a cream or lotion.

The compositions according to the invention are preferably used in the form of products to be rinsed through, before and more particularly after shampooing, before and more particularly after dyeing or bleaching, before and more particularly after a perm or straightening. It has been found that these compositions are stable in the course of time, even in the presence of cationic surface-active agents, which was not previously foreseeable by the expert in the art taking account in particular of the indications contained in the patent US-A-3 957 971 (column 11, line 1). In addition, these compositions have a collection of cosmetic properties which are advantageous over the prior art and all the more interesting and surprising because their effect is immediate, that is to say that it is not necessary for the user to leave the composition to rest on the hair before rinsing, resulting a very appreciable saving of time and more convenient use. Nevertheless, it remains possible to leave the composition for some time before rinsing without changing the good properties which are obtained.

These compositions do not make the hair greasy, do not weaken the hair, makes it untangle easily and makes it easy to comb when damp or dry.

The said compositions also give the hair surprising properties such as uniform gloss, a lightness and a great softness from the root to the tip. A surprising effect of individualisation of the capillary fibers and a significant reduction in the static electricity is noted. These properties are obtained on hair or which has not been rendered very sensitive when the composition does not contain any cationic surface-active agent and also on sensitive hair when the composition does contain a cationic surface-active agent.

These compositions are also very easily eliminated by rinsing with water.

The third object of the present invention is a process of cosmetic treatment of the hair, characterised in that an effective quantity of the composition according to the invention is applied to the hair, the hair is optionally combed and finally the hair is rinsed.

Using this treatment, quantities of compositions generally of the order of 5 to 40 g are applied to the head.

The examples given below, which are given purely by way of illustration and are not limiting, will make it possible to understand the invention better.

EXAMPLE 1

In a first stage a first constituent comprising vesicles is prepared. For this, a mixture of 10.8 g of nonionic lipids of formula:

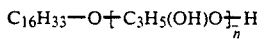

where n is a mean statistical value equal to 3, and $C_3H_5(OH)O$ is represented by the mixture of the following structures:

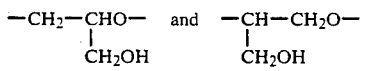

are melted at a temperature of 95° C. with 1.2 g of stearyl monosodium glutamate salt sold under the brand name "ACYLGLUTAMATE HS 11" by "AJINOMOTO". Then 28.6 g of a mixture containing 13% by weight of a polydimethylsiloxane hydroxylated at the end of the chain associated with 87% by weight of a mixture of octamethylcyclotetrasiloxane and decamethylcyclopentasiloxane sold under the brand name "Q2 1401" by "DOW CORNING" are added to the melted mixture and simultaneously the mixture is subjected to mixing with gentle agitation for 5 minutes (time necessary for perfect homogenisation).

103 g of water brought to 90° C. and containing a preservative are introduced into the melted mixture, and mixing is carried out for approximately 5 minutes. 154 g of water at 20° C. are added to the phase thus obtained and the mixture is agitated for several minutes; it is then completed by 461 g of water at 20° C. and the mixture is refined by passing it through a high-pressure homogeniser at 500 bars of the "RANNIE" type.

In a second stage a second constituent comprising the aqueous dispersion phase is prepared; in order to do this, 25.6 g of an 80% solution of active material (for instance 22 g of active material) of a quaternary ammonium salt sold under the brand name "REWOQUAT W 7500" by "REWO" is dissolved for 10 minutes at 80° C. in 141 g of water.

The first and second constituents thus obtained are mixed and are homogenised under gentle agitation.

When the temperature reaches approximately 40° C. the perfume is added, then the mixture is made up to 1000 g with water at ambient temperature and agitated gently until it returns to ambient temperature, A composition is obtained which has the appearance of a cream. It was observed that this composition was stable after three months at ambient temperature by verifying the presence of the vehicles by electron microscopy.

This composition is applied in a quantity of about 15 g to sensitive hair which has been washed and partly dried. It is rinsed copiously with water several seconds after the end of the application.

The damp hair untangles easily; it is smooth and soft from the root to the tip. After drying it is bouncy and combs very easily; it is not electric it is shiny, smooth and supple over its entire length. The hairstyle is light and full of body.

EXAMPLE 2

Example 1 is reproduced by replacing the nonionic lipid by that of the following formula:

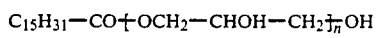

in which n is equal to 2.

A stable composition is obtained which has the same cosmetic properties on the hair as the composition of example 1.

EXAMPLE 3

The product sold under the brand name "REWOQUAT W 7500" by "REWO" is replaced in example 1 by an equal quantity of distearyldimethylammonium. A stable composition is obtained which has the same cosmetic properties on the hair as the composition of example 1.

In the examples 4 to 6 below, the process is carried out as in example 1 except that the silicone sold under the brand name "Q2 1401" by "DOW CORNING" is replaced by other silicones in equal quantities.

EXAMPLE 4

The silicone is a mixture of 15% by weight of the product sold under the brand name "SILBIONE 47V500000" by "RHONE POULENC" in 85% by weight of the product sold under the brand name "VOLATILE SILICONE 7158" by 37 UNION CARBIDE".

EXAMPLE 5

The silicone is a mixture of 15% by weight of a polydimethylsiloxane (with a molecular weight of 600000) hydroxylated at the end of the chain in 85% by weight of a mixture of decamethylcyclopentasiloxane and octamethylcyclotetrasiloxane (50/50 ).

EXAMPLE 6

The silicone is a mixture of 15% by weight of phenylmethylsiloxane (with a molecular weight of 600000) in 85% of a mixture of decamethylcyclopentasiloxane and octamethylcyclotetrasiloxane (50/50).

For each of the examples 4 to 6 defined above, stable compositions are obtained which have the same cosmetic properties as the composition of example 1.

EXAMPLE 7

The process is carried out as in example 1 in order to obtain the following composition:

| | |
|---|---|
| Nonionic compound of formula IV (see below) | 3.63 g |
| Cholesterol | 0.97 g |
| Silicone sold under the brand name "Q2 1401" by "DOW CORNING" | 2.86 g |
| Cationic surface-active agent sold under the brand name "REWOQUAT W 7500" by "REWO" at 80% active material (AM) (in AM) | 2.20 g |
| preservative q.s. | |
| water q.s.p. | 100.00 g |

Formula IV is as follows:

$$C_{12}H_{25}\!-\!\!\left[OC_2H_3(R_{10})\right]\!-\!\!\left[O\!-\!C_3H_5(OH)\!-\!O\right]_{\overline{n}}\!H$$

in which: —O—$C_2H_3(R_{10})$— is constituted by a mixture of radicals:

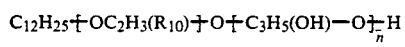

—$C_3H_5(OH)$—O— is constituted by a mixture of radicals:

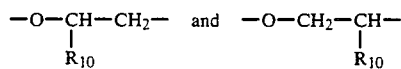

$\overline{n}=6$, and $R_{10}$ is a mixture of the radicals:
$C_{14}H_{29}$— and $C_{16}H_{33}$—

EXAMPLE 8

In this example the activity of two compositions A and B which contain the same quantities of the same silicone and do not contain any cationic surface-active agent are compared. The composition A according to the invention contains nonionic amphiphilic lipids in the form of vesicles and composition B, which does not conform to the invention, contains nonionic amphiphilic lipids which do not form vesicles, the quantities of lipids A and B being the same.

The formulations are as follows:

| | Composition A | Composition B |
|---|---|---|
| Amphiphilic lipids according to the invention (in total): in the form of a mixture of: | 2.28 g | |
| Nonionic lipid of example 1 | 1.08 g | |
| Cholesterol | 1.08 g | |
| Monosodium glutamate salt sold under the brand name "ACYLGLUTAMATE HS 11" | 0.12 g | |
| Nonionic lipids not conforming to the invention (in total): in the form of a mixture of: | | 2.28 g |
| Sorbitan stearate Polysorbate 60 Mixture of cetylstearyl alcohols and oxyethylene cetyl stearyl alcohols (15 moles of ethylene oxide) | | in proportions 0.23/ 0.15/1.90 |
| Silicone sold under the brand name "Q2 1401" by "DOW CORNING" | 2.86 g | 2.86 g |
| Preservative q.s. | | |
| Water q.s.p. | 100 g | 100 g |

The compositions A and B were applied simultaneously in a quantity of 6 g to half a head on clean wet hair. The whole head of hair was rinsed with tepid water, the hair was combed and dried. Then the state of the hair on the two halves of the head were compared. These tests were carried out on natural hair which had not been rendered very sensitive, on permed hair and on dyed permed hair.

For all the hair treated the composition A gives an effect of glossiness, of hold and of covering which is not obtained with composition B. Moreover, composition A reduces the phenomenon of formation of electrostatic electricity and this effect is retained after shampooing. In the case of natural hair which has not been rendered very sensitive, an effect of untangling and softness and light hair is obtained with composition A which is not obtained with composition B, which by contrast makes the hair heavy.

EXAMPLE 9

In this example, the activity of two compositions C and D is compared, these two compositions having the same formulation as compositions A and B except that 2.2 g of the cationic surface-active agent sold under the brand name "REWOQUAT W 7500" by "DOW CORNING" are added in the two compositions.

The process for application is the same in both cases: 15 g of composition is spread over an entire head of hair which has been permed. It rinsed with tepid water; the hair is combed and dried.

It is noted that composition C has a better untangling effect and gives the hair more softness and shine than composition D, which incidentally makes the hair greasy and heavy.

EXAMPLE 10

The first stage is carried out according to example 1.

In a second stage, a second constituent is prepared including the ingredients of the aqueous dispersion phase: in order to do this, 25.6 g of the cationic surface-active agent sold under the brand name "REWOQUAT W 7500" by "REWO" are brought to a temperature of 80° C. 51.20 g of water brought to 80° C. are introduced into the melted mixture and mixing is carried out for approximately 5 minutes. 76.8 g of water at 20° C. are added to the phase thus obtained. The mixture is agitated for several minutes, then 13 g of water at 20° C. are added. The mixture is introduced into a high-pressure homogeniser at 500 bars of the "RANNIE" type.

The first and second constituents thus obtained are mixed under gentle agitation at ambient temperature. The perfume is added, then the mixture is made up to 1000 g with water at ambient temperature under gentle agitation.

This composition is more particularly adapted to hair with a tendency to greasiness. It makes the hair light, gentle and shiny.

EXAMPLE 11

In a first stage a first constituent comprising vesicles is prepared. For this, a mixture of 10.9 g of nonionic lipids of formula:

$$C_{16}H_{33}-O+C_3H_5(OH)O+_nH$$

where n is a mean statistical value equal to 3, and $C_3H_5(OH)O$ is represented by the mixture of the following structures:

$$-CH_2-CHO \quad \text{and} \quad -CH-CH_2O-$$
$$\phantom{-CH_2-}| \phantom{CHO \quad \text{and} \quad -CH-}|$$
$$\phantom{-CH_2-}CH_2OH \phantom{\quad \text{and} \quad -CH-}CH_2OH$$

are melted at a temperature of 95° C. with 10.9 g of cholesterol and 1.2 g of stearyl monosodium glutamate salt sold under the brand name "ACYLGLUTAMATE HS 11" by "AJINOMOTO". Then 0.4 g of a mixture containing 13% by weight of a polydimethylsiloxane hydroxylated at the end of the chain associated with 87% by weight of a mixture of octamethylcyclotetrasiloxane and decamethylcyclopentasiloxane sold under the brand name 37 Q2 1401" by "DOW CORNING", 42.5 g of decamethylcyclopentasiloxane sold under the brand name "SILBIONE huile 70045V5" by "RHONE POULENC", 7.5 g of polydimethylsiloxane sold under the brand name "SILBIONE 47V500000" by "RHONE POULENC" are added to the melted mixture and simultaneously the mixture is subjected to mixing with gentle agitation for 5 minutes (time necessary for perfect homogenisation).

147 g of water brought to 90° C. and containing a preservative are introduced into the melted mixture, and mixing is carried out for approximately 5 minutes. 220 g of water at 20° C. are added to the phase thus obtained and the mixture is agitated for several minutes; it is then completed by 300 g of water at 20° C. and the mixture is refined by passing it through a high-pressure homogeniser at 500 bars of the "RANNIE" type.

In a second stage a second constituent comprising the aqueous dispersion phase is prepared; in order to do this, 62.5 g of a 75% solution of active material (for instance 46.9 g of active material) of a quaternary ammonium salt sold under the brand name "REWOQUAT W 7500" by "REWO" are dissolved for 10 minutes at 80° C. in 141 g of water.

The first and second constituents thus obtained are mixed and are homogenised under gentle agitation. Then 2.5 g of hydroxyethylcellulose modified by an alkyl chain sold under the brand name "NATROSOL PLUS GRADE 330 CS" by 37 AQUALON" dissolved in 50 g of water at 80° C. are added to the mixture as thickener.

When the temperature reaches approximately 40° C. the perfume is added, then the mixture is made up to 1000 g with water at ambient temperature and agitated gently until it returns to ambient temperature.

A composition is obtained which has the appearance of a cream.

This composition is applied in a quantity of about 15 g to sensitive hair which has been washed and partly dried. It is rinsed copiously with water several seconds after the end of the application.

The damp hair untangles easily; it is smooth and soft from the root to the tip. After drying it is bouncy and combs very easily; it is not electric; it is shiny, smooth and supple over its entire length. The hairstyle is light and full of body.

We claim:

1. A process for producing a cosmetic composition for application to the hair, said composition comprising in an aqueous dispersion phase a dispersion of vesicles comprising at least one nonionic amphiphilic lipid capable of forming vesicles and at least one water-insoluble, volatile or non-volatile silicone in the form of an oil, gum or resin, said nonionic amphiphilic lipid being present in said composition in an amount ranging from 1 to 20 weight percent based on the total weight of said composition and said silicone being present in an amount ranging from 0.5 to 10 weight percent based on the total weight of said composition, said process comprising
   (a) admixing said nonionic amphiphilic lipid capable of forming vesicles with said water-insoluble volatile or non-volatile silicone,
   (b) mixing the mixture resulting from step (a) with an aqueous phase to be encapsulated in the vesicles to be formed and agitating the resulting mixture until said vesicles are formed, and
   (c) dispersing the formed vesicles in an aqueous phase, said nonionic amphiphilic lipid being a linear or branched ether or ester of polyglycerol having the formula $$, RO-[-C_3H_5(OH)-O-]_n-H$$

wherein
—$C_3H_5(OH)$—O— represents in a mixture or separately —$CH_2$—$CHOHCH_2$—O—

$$-CH-CH_2O- \quad \text{and} \quad -CH_2-CHO-,$$
$$\phantom{-CH-}| \phantom{CH_2O- \quad \text{and} \quad -CH_2-}|$$
$$\phantom{-CH-}CH_2OH \phantom{\quad \text{and} \quad -CH_2-}CH_2OH$$

n has a mean statistical value ranging from 2 to 6, and R represents either
(a) an aliphatic chain $R_1$ or an $R_2CO$ radical wherein $R_1$ is a linear or branched $C_{12}$-$C_{17}$ aliphatic radical and $R_2$ is a linear or branched $C_{11}$-$C_{17}$ aliphatic radical, or
(b) $R_3$ [$OC_2H_3(R_4)$], wherein —$OC_2H_3(R_4)$— represents, in a mixture or separately, $$-O-CH-CH_2- \quad \text{and} \quad -O-CH_2-CH-,$$
$$\phantom{-O-}| \phantom{CH-CH_2- \quad \text{and} \quad -O-CH_2-}|$$
$$\phantom{-O-}R_4 \phantom{CH-CH_2- \quad \text{and} \quad -O-CH_2-}R_4$$

wherein $R_3$ is $R_1$ and $R_2CO$ and $R_4$ is $R_1$, wherein $R_1$ and $R_2$ have the meanings given above wherein said water-insoluble volatile or non-volatile silicone is selected from the group consisting of a polydimethylsiloxane, a mixture of a polydimethylsiloxane and a trimethylsiloxysilicate, a polydimethylsiloxane modified by a hydroxyl group at the end of the chain, a polydimethylsiloxane modified by a $C_{12}$-$C_{22}$ alkoxy group, a polydimethylsiloxane modified by a polyoxyalkylene group wherein the alkylene moiety has 2-3 carbon atoms, a polydimethylsiloxane modified by an acyloxyalkyl radical wherein the acyl moiety has 12-22 carbon atoms and the alkyl moiety has 1-4 carbon atoms, a polydimethylphenylsiloxane, a polymethylalkylsiloxane wherein the alkyl moiety has 20 carbon atoms, a polymethylalkylarylsiloxane, wherein the alkyl moiety has 1-4 carbon atoms, modified by an alkylamine group wherein the alkyl moiety has 1-4 carbon atoms, and a cyclopolysiloxane, and wherein non-volatile silicone is in solution in at least one cyclic volatile silicone oil.

2. The process of claim 1 wherein said aqueous phase containing said dispersion of vesicles also contains at least one cationic surface-active agent in an amount ranging from 1 to 10 weight percent based on the total weight of said composition
wherein said cationic surface active agent is a quaternary ammonium derivative having the formula

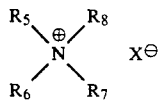

wherein

X is chlorine or $CH_3SO_4$ and $R_5$ is a $C_1$-$C_4$ alkyl, and
wherein either $R_6$ and $R_7$ are a $C_1$-$C_4$ alkyl radical, identical to or different from $R_5$ and each other, and $R_8$ is a $C_{20}$-$C_{22}$ radical; or $R_6 = R_5$ and $R_7 = R_8 = C_{18}$ alkyl radical, or $R_6$ represents an alkyl amidoethyl radial, an alkenyl amidoethyl radical or an alkylalkenylamido ethyl radical wherein said alkyl and alkenyl moieties have 13-21 carbon atoms and derived from the fatty acids of tallow; and $R_7$ and $R_8$ together with nitrogen atom to which they are attached form a 4,5-dihydroimidazole heterocycle which is substituted, in position 2, by a $C_{13}$-$C_{21}$ alkyl or alkenyl radical or both.

3. The process of claim 1 wherein forming said vesicles comprises melting said mixture of said nonionic amphiphilic lipid capable of forming vesicles and said water-insoluble volatile or non-volatile silicone, adding said aqueous phase to be encapsulated in said vesicles to said melted mixture so as to form a hydrated lamellar phase and continuing the addition of said aqueous phase to be encapsulated under energetic agitation so as to form said vesicles.

4. The process of claim 1 wherein forming said vesicles comprises dissolving said nonionic amphiphilic lipid capable of forming vesicles and said water-insoluble volatile or non-volatile silicone in an organic solvent in a receptacle, evaporating said solvent so as to form a film of a mixture of said lipid and said silicone on the wall of said receptacle, and adding to said receptacle said aqueous phase to be encapsulated in said vesicles under energetic agitation so as to form said vesicles.

5. The process of claim 3 which includes adding at least one stabilizing additive to said nonionic amphiphilic lipid so as to modify the permeability or surface charge of said hydrated lamellar phase.

6. The process of claim 1 which includes adding to said nonionic amphiphilic lipid or to said silicone or to both a substance selected from the group consisting of at least one liposoluble cosmetically active substance, at least one liposoluble pharmaceutically active substance, and a mixture thereof.

7. The process of claim 1 which includes adding to said aqueous phase to be encapsulated in said vesicles or to the aqueous phase in which said vesicles are dispersed or both a substance selected from the group consisting of at least one water-soluble cosmetically active substance, at least one water-soluble pharmaceutically active substance, and a mixture thereof.

8. The process of claim 1 which includes adding to said aqueous phase to be encapsulated in said vesicles or to the aqueous phase in which said vesicles are dispersed a compound selected from the group consisting of a preservative, a coloring agent, perfume, and a mixture thereof.

9. The process of claim 1 which includes adding a thickening agent to the aqueous phase in which said vesicles are dispersed.

10. The process of claim 1 which includes adding a water-immiscible substance to the aqueous phase in which said vesicles are dispersed.

11. A composition obtained in accordance with the method of claim 1, said composition comprising in an aqueous dispersion phase, a dispersion of vesicles comprising at least one nonionic amphiphilic lipid capable of forming vesicles and at least one water-insoluble volatile or nonvolatile silicone wherein said at least one water-insoluble volatile or nonvolatile silicone is selected from the group consisting of an oil, a gum, and a resin.

12. The composition of claim 11 wherein said aqueous dispersion phase contains at least one cationic surface active agent.

13. The composition of claim 11 containing by weight with respect to the total weight of said composition
1 to 7 percent of said cationic surface-active agent,
1.5 to 10 percent of said nonionic amphiphilic lipid and 1.5 to 5 percent of said silicone.

14. A process for the cosmetic treatment of the hair comprising applying to said hair an effective amount of the composition of claim 11, optionally combining the hair and then rinsing the hair.

* * * * *